US009250189B1

(12) United States Patent
Johnson

(10) Patent No.: US 9,250,189 B1
(45) Date of Patent: *Feb. 2, 2016

(54) COLORIMETRIC TEST KIT

(71) Applicant: Field Forensics, Inc., St. Petersburg, FL (US)

(72) Inventor: Craig R Johnson, Tierra Verde, FL (US)

(73) Assignee: Field Forensics, Inc., St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/894,855

(22) Filed: May 15, 2013

Related U.S. Application Data

(60) Provisional application No. 61/647,270, filed on May 15, 2012.

(51) Int. Cl.
  *G01N 21/78* (2006.01)
  *G01N 1/02* (2006.01)

(52) U.S. Cl.
  CPC ........ *G01N 21/78* (2013.01); *G01N 1/02* (2013.01); *G01N 2001/028* (2013.01)

(58) Field of Classification Search
  CPC .............................. B01L 3/5029; G01N 21/76
  USPC .......................................... 422/402, 430, 500
  See application file for complete search history.

(56) References Cited

U.S. PATENT DOCUMENTS

| | | | | |
|---|---|---|---|---|
| 6,197,254 B1* | 3/2001 | Silver et al. | ..................... | 422/52 |
| 6,372,511 B1* | 4/2002 | Silver et al. | ................... | 436/165 |
| 6,927,851 B2* | 8/2005 | McCaffrey et al. | ........... | 356/311 |
| 8,845,978 B2* | 9/2014 | Johnson | ....................... | 422/430 |
| 2008/0018894 A1* | 1/2008 | Zu et al. | ........................ | 356/338 |
| 2014/0093969 A1* | 4/2014 | Johnson | ........................ | 436/103 |

OTHER PUBLICATIONS

Northeastern University. "Northeastern University Physicists Become First to Demonstrate Flat Lens Imaging." ScienceDaily. ScienceDaily, Dec. 2, 2003. <http://www.sciencedaily.com/releases/2003/12/031202065957.htm>.*
Aieta, Francesco et al. "Aberration-Free Ultrathin Flat Lenses and Axicons at Telecom Wavelengths Based on Plasmonic Metasurfaces," Nano Lett., 2012, 12 (9), pp. 4932-4936.*
Current online definition of "magnifying glass." Feb. 5, 2015. <http://en.wiktionary.org/wiki/magnifying_glass>.*

* cited by examiner

*Primary Examiner* — Dennis M White
*Assistant Examiner* — Bryan Kilpatrick
(74) *Attorney, Agent, or Firm* — Christopher Paradies; Paradies Law P.A.

(57) ABSTRACT

A detection kit is used for detecting compounds and includes a magnifying lens in a cap that magnifies a surface of a color-changing detection swab when placed on the body of the detection kit. For example, the cap includes a plurality of lenses that are integrally formed in a plastic cap, and each lens magnifies the surface of a different swab.

7 Claims, 3 Drawing Sheets

COLORIMETRIC TEST KIT

RELATED APPLICATION

This application is a non-provisional which claims the benefit of the filing date of U.S. Provisional Application No. 61/647,270 filed May 15, 2012, which is incorporated herein in its entirety.

FIELD OF THE INVENTION

The invention relates to test kits that use a change in color or darkness for identifying substances.

BACKGROUND

International Application No. PCT/US2011/053925 of applicant discloses the background and is incorporated herein in its entirety.

SUMMARY OF THE INVENTION

A detection kit includes a cover having at least one magnifier lens, each incorporated into the cover to magnify the detection surface of a particular detection surface. The magnifier improves the visibility to a person viewing any chemical change on the surface of the detector, such as the surface of a swab used in detecting compounds, such as chemical agents, explosives, elements of explosive devices or improvised explosive devices and illegal substances, such as illegal drugs, unlicensed or unregistered chemicals or chemicals used in making illegal drugs.

In one example, the cap is molded integrally as a portion of the cap. For example, the entire cap may be a transparent plastic material, such as a polycarbonate, polypropylene or acrylic. Alternatively, the magnifying lens may be provided by a pop-in lens mechanically fitted into the cap. In yet another alternative, the lens effect may be provided by a diffraction grating. In yet another alternative, the lens effect is provided by a ball lens, such as a glass ball lens.

For example, the lens effect increases the threshold of detection of a color change on a surface of swab-type of a chemical detector. For example, the swab may be fluidically coupled with an ampoule in a detector, such that when the ampoule is broken or crushed, the fluid from the ampoule wets the swab surface resulting in a color change if a particular chemical is disposed on the swab surface after swabbing the swab surface on a surface to be examined for trace chemical detection.

BRIEF DESCRIPTION OF THE DRAWINGS

The examples illustrated in the following drawings and the detailed description are examples of the invention for the purpose of illustrating features of the invention to be recited in the claims of an issued patent and are not limiting to the scope of the inventions claimed.

DETAILED DESCRIPTION

Figure 1:
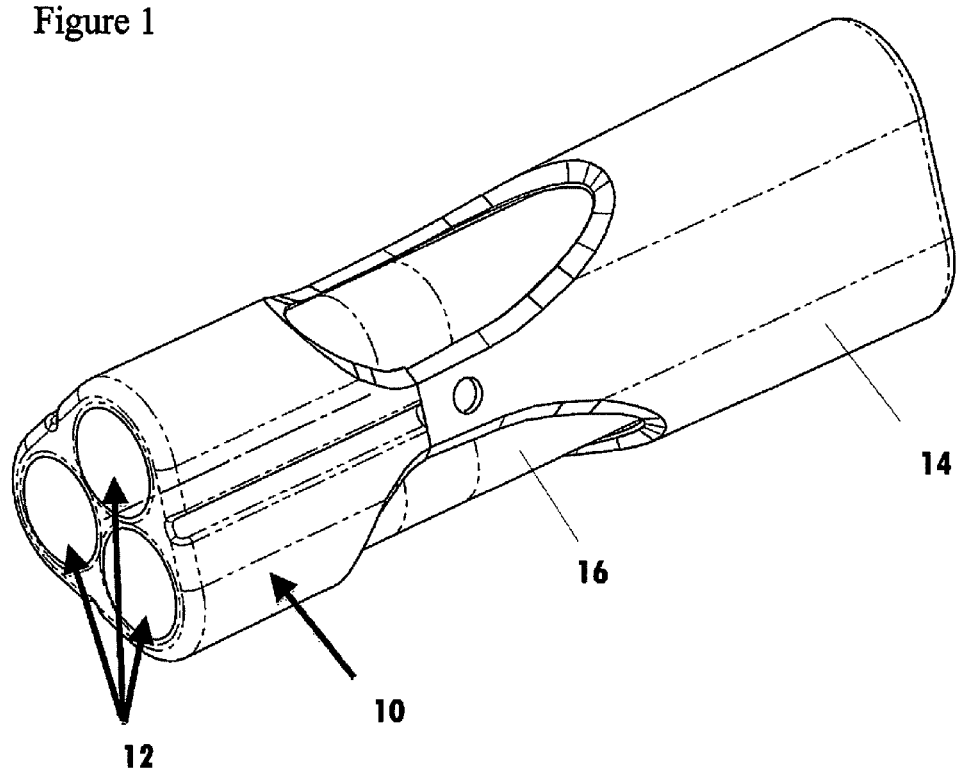
FIG. 1 illustrates a multi-detector having three lenses integrally formed into a transparent plastic lens cap.

FIG. 1 illustrates an example of a plurality of lenses 12 (e.g. three) integrally formed in a transparent plastic lens cap 10 disposed on a multi-detector colorimetric test kit 14 having three swab surfaces disposed directly below the lenses, when the lens cap is disposed onto the multi-detector. Each sampling tip of the multi-detector 16 is magnified by its own lens, for example.

Figure 2:
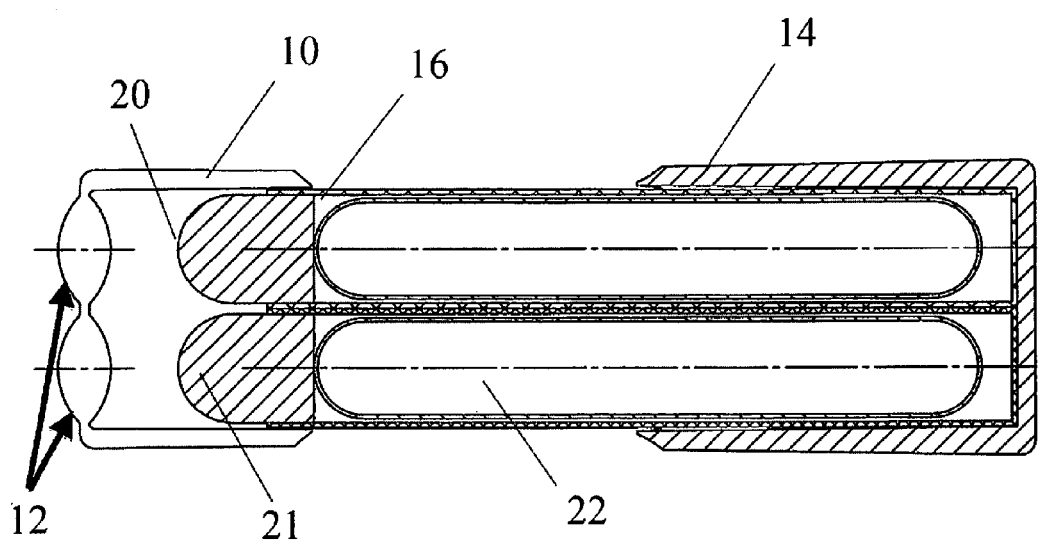
FIG. 2 illustrates a side cross sectional view through two lenses in a lens cap used with a multi-detector.

FIG. 2 illustrates a cross section view with the lens cap 10 in position on a multi-detector 16 having a plurality of lenses 12 (e.g. two shown). The colorimetric test kit 14 includes an ampoule 22 having a solvent or liquid capable of causing a reaction on the surface 20 of each tip 21 if a particular trace chemical is disposed on the surface 20 of the tip 21, such as during swabbing of a contaminated surface with the multi-detector swab 16 tips 21.

Figure 3A:
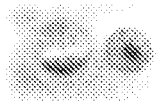
FIGS. 3A and 3B illustrate (A) a view of a detection surface before disposing a glass ball lens over the detection surface and (B) a view of the detection surface with the glass ball lens positioned directly over the detection surface.
Figure 3B:
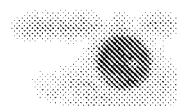

In FIGS. 3A and 3B a dramatic advantage of using a lens in a lens cap is shown by the glass ball lens, which magnifies the small grain of color change in FIG. 3A to fill the magnified view in FIG. 3B. By integrating a lens in a cover used in a detector kit, the lens provides much improved visibility of any color change caused by a chemical reaction on the detection surface of a colorimetric detection kit. This allows a lower threshold of detection for the kit without using more complex chemical processes and procedures to induce a higher contrast on the surface. Therefore, a less costly and easier to use kit is capable of providing trace chemical and biological detection.

The claims are not limited to the examples, and features of the examples may be combined or modified by a person having ordinary skill in the art, based on this description and the drawings provided. The examples are provided to show various arrangements and features, and the arrangement and features in one example may be combined with the arrangement and features of other examples.

What is claimed is:

1. A detection kit for detecting compounds, the kit comprising:
   a body having an engaging end;
   a cap having a first end, a second end opposite of the first end, and a lens disposed on the first end, and when the cap engages the body, the second end of the cap engages the engaging end of the body of the detection kit; and
   a swab, disposed in the body of the detection kit and having a tip, the tip having a detection surface for detecting compounds, the detection surface extending beyond the engaging end of the body such that the detection surface is capable of making contact with a surface to be tested when the cap is removed from the body of the detection kit, and the tip is arranged within the body and in relation to the lens, wherein at least a portion of the tip is magnified by the lens when the cap is disposed on the body of the kit,
   wherein the swab includes at least two swabs and the lens includes at least two lenses, each of the two lenses being disposed in the cap, such that the respective surfaces of the at least two swabs are magnified by a respective one of the at least two lenses.

2. The kit of claim 1, wherein a first of the at least two swabs includes a solvent or liquid capable of causing a reaction on the surface of the first of the at least two swabs for detecting one or more of the compounds, and a second of the at least two swabs includes a different solvent or liquid capable of causing a different reaction to occur on the surface of the second of the at least two swabs than the reaction that occurs on the surface of the first of the at least two swabs.

3. The kit of claim 1, wherein at least one of the two lenses increases a threshold of detection of a color change on the detection surface of one of the at least two swabs.

4. The kit of claim 1, wherein one of the at least two lenses is a glass ball or bead.

5. The kit of claim 1, wherein at least one of the at least two lenses is integrally formed with the cap.

6. The kit of claim 5, wherein the cap is formed of a plastic.

7. The kit of claim 6, wherein a shape of a lower body of the cap is selected to conform to a shape of an upper portion of a body enclosing the swab, such that the lower body of the cap fits onto the upper portion and is retained thereon.

* * * * *